(12) United States Patent
Hsieh et al.

(10) Patent No.: US 6,944,260 B2
(45) Date of Patent: Sep. 13, 2005

(54) METHODS AND APPARATUS FOR ARTIFACT REDUCTION IN COMPUTED TOMOGRAPHY IMAGING SYSTEMS

(75) Inventors: Jiang Hsieh, Brookfield, WI (US); Edward Henry Chao, Oconomowoc, WI (US); Brian James Grekowicz, Waukesha, WI (US); Jean-Baptiste Thibault, Milwaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 97 days.

(21) Appl. No.: 10/705,357

(22) Filed: Nov. 11, 2003

(65) Prior Publication Data

US 2005/0100124 A1    May 12, 2005

(51) Int. Cl.$^7$ ................................................ A61B 6/03
(52) U.S. Cl. ............................. 378/19; 378/4; 378/901
(58) Field of Search .......................... 378/4, 8, 15, 19, 378/901

(56) References Cited

U.S. PATENT DOCUMENTS

| | | | |
|---|---|---|---|
| 6,115,487 A | 9/2000 | Toth et al. |
| 6,134,292 A | 10/2000 | Hsieh |
| 6,215,841 B1 | 4/2001 | Hsieh |
| 6,233,308 B1 | 5/2001 | Hsieh |
| 6,408,042 B1 | 6/2002 | Hsieh |
| 6,421,411 B1 | 7/2002 | Hsieh |
| 6,438,195 B1 | 8/2002 | Hsieh |
| 6,507,632 B1 | 1/2003 | Hsieh |
| 6,529,574 B1 | 3/2003 | Hsieh |
| 6,570,951 B1 | 5/2003 | Hsieh |
| 2003/0031289 A1 | 2/2003 | Hsieh |

*Primary Examiner*—David V Bruce
(74) *Attorney, Agent, or Firm*—Carl B. Horton, Esq.; Armstrong Teasdale, LLP

(57) ABSTRACT

Some configurations of the present invention provide a method for reconstructing an image of an object of a computed tomographic imaging system having a detector array and a radiation source, wherein an arc of the detector array is not concentric to a focal spot of the radiation source. The method includes scanning the object with the computed tomographic imaging system to obtain a fan beam dataset, rebinning the fan beam dataset into a set of parallel datasets; and reconstructing an image utilizing the set of parallel datasets.

28 Claims, 6 Drawing Sheets

METHODS AND APPARATUS FOR ARTIFACT REDUCTION IN COMPUTED TOMOGRAPHY IMAGING SYSTEMS

BACKGROUND OF THE INVENTION

This invention relates generally to computed tomography (CT) imaging, and more particularly, to methods and apparatus for artifact reduction in a CT systems that are particularly useful for such systems having a wide bore geometry.

In many clinical applications of computed tomography imaging, a larger gantry opening is useful. For example, in oncology applications, a large bore size allows a patient to be positioned in fashion similar to the position of a patient in a radiation treatment machine, which typically has a large opening. When computed tomography scanners are used to aid in performing interventional procedures, an operator's access to a patient is limited by the bore size. In at least one known computed tomography system, both the x-ray tube and the detector are positioned away from the isocenter to increase the operator's access. However, to save development cost as well as flexibility of an adjustable geometry, a detector designed for the original geometry is used, rendering the arc of the detector of the imaging device no longer concentric to a focal spot of the x-rays. As a result, image artifacts are introduced in reconstructed images because the x-ray path is no longer the original path assumed by the reconstruction process.

BRIEF DESCRIPTION OF THE INVENTION

There is therefore provided, in some configurations of the present invention, a method for reconstructing an image of an object of a computed tomographic imaging system having a detector array and a radiation source, wherein an arc of the detector array is not concentric to a focal spot of the radiation source. The method includes scanning the object with the computed tomographic imaging system to obtain a projection dataset, performing a geometric correction of the projection dataset according to a corrected fan angle; and reconstructing an image utilizing the corrected projection dataset.

Various configurations of the present invention also provide a method for reconstructing an image of an object of a computed tomographic imaging system having a detector array and a radiation source, wherein an arc of the detector array is not concentric to a focal spot of the radiation source. The method includes scanning the object using step-and-shoot scanning with the computed tomographic imaging system, without applying a weighting function, to obtain a projection dataset, rebinning the projection dataset into a set of parallel datasets. An image is reconstructed utilizing the set of parallel datasets.

Still other configurations of the present invention provide a method for reconstructing an image of an object of a computed tomographic imaging system having a detector array and a radiation source, wherein an arc of the detector array is not concentric to a focal spot of the radiation source. These methods include scanning the object with the computed tomographic imaging system using helical or halfscan acquisition to obtain a projection dataset. The projection dataset is weighted in accordance with a weighting function w', derived from a weighting function w for an original geometry in which the arc of the detector array is concentric to the focal spot of the radiation source. The method further includes rebinning the projection dataset into a set of parallel datasets and reconstructing an image utilizing the set of parallel datasets.

In yet another aspect of the present invention, there is provided a computed tomography imaging system having a detector array and a radiation source, wherein an arc of the detector array is not concentric to a focal spot of the radiation source. The imaging system is configured to scan an object to obtain a projection dataset, perform a geometric correction of the projection dataset according to a corrected fan angle, and reconstruct an image utilizing the corrected projection dataset.

In still other configurations of the present invention, there is provided a computed tomography imaging system having a detector array and a radiation source, wherein an arc of the detector array is not concentric to a focal spot of the radiation source. The imaging system is configured to scan the object using step-and-shoot scanning without applying a weighting function to obtain a projection dataset, rebin the projection dataset into a set of parallel datasets, and reconstruct an image utilizing the set of parallel datasets.

Various configurations of the present invention provide a computed tomography imaging system having a detector array and a radiation source, wherein an arc of the detector array is not concentric to a focal spot of the radiation source. The imaging system is configured to scan the object using helical or halfscan acquisition to obtain a projection dataset and weight the projection dataset in accordance with a weighting function w', derived from a weighting function w for an original geometry in which the arc of the detector array is concentric to the focal spot of the radiation source. The imaging system is further configured to rebin the projection dataset into a set of parallel datasets and reconstruct an image utilizing the set of parallel datasets.

Configurations of the present invention are useful in reducing artifacts in reconstructed images when a larger gantry bore is desired. Development cost is reduced while maintaining the flexibility of an adjustable geometry by allowing a detector designed for the original geometry to be used. Image artifacts that would otherwise be introduced in reconstructed images are reduced by configurations of the present invention.

DETAILED DESCRIPTION OF THE INVENTION

Figure 1:
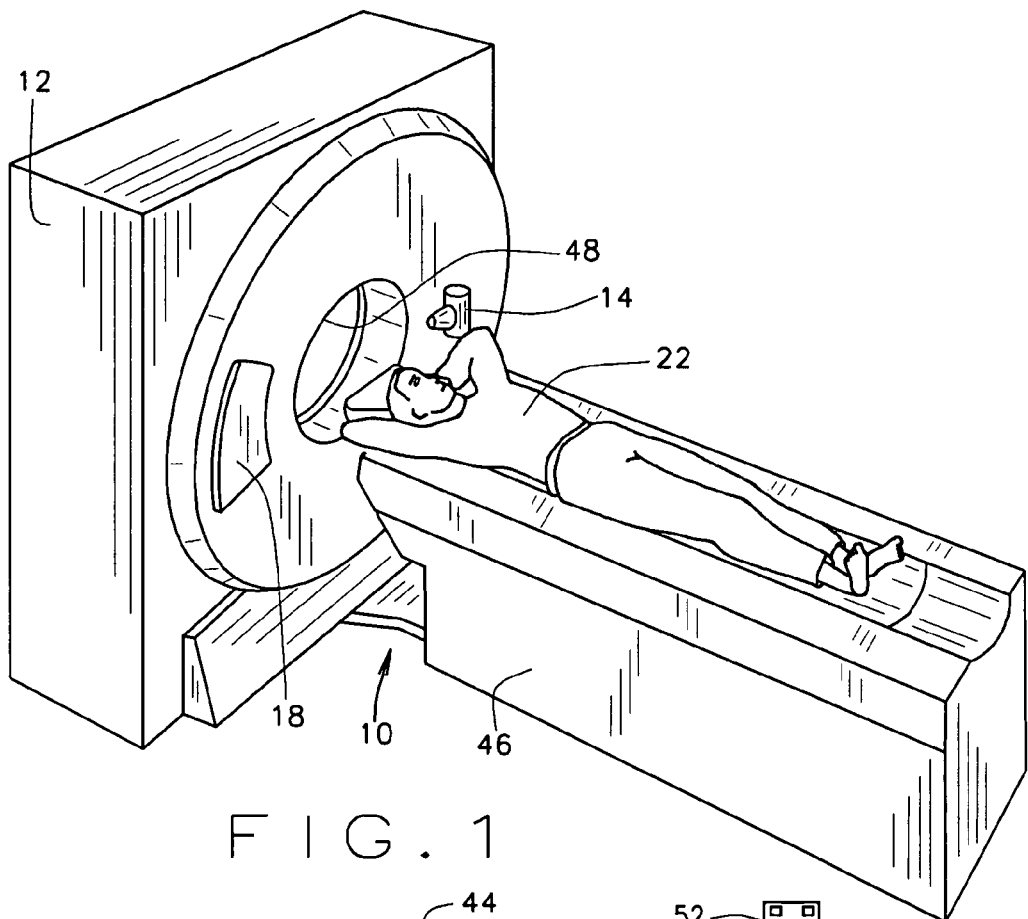
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube or other type of display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
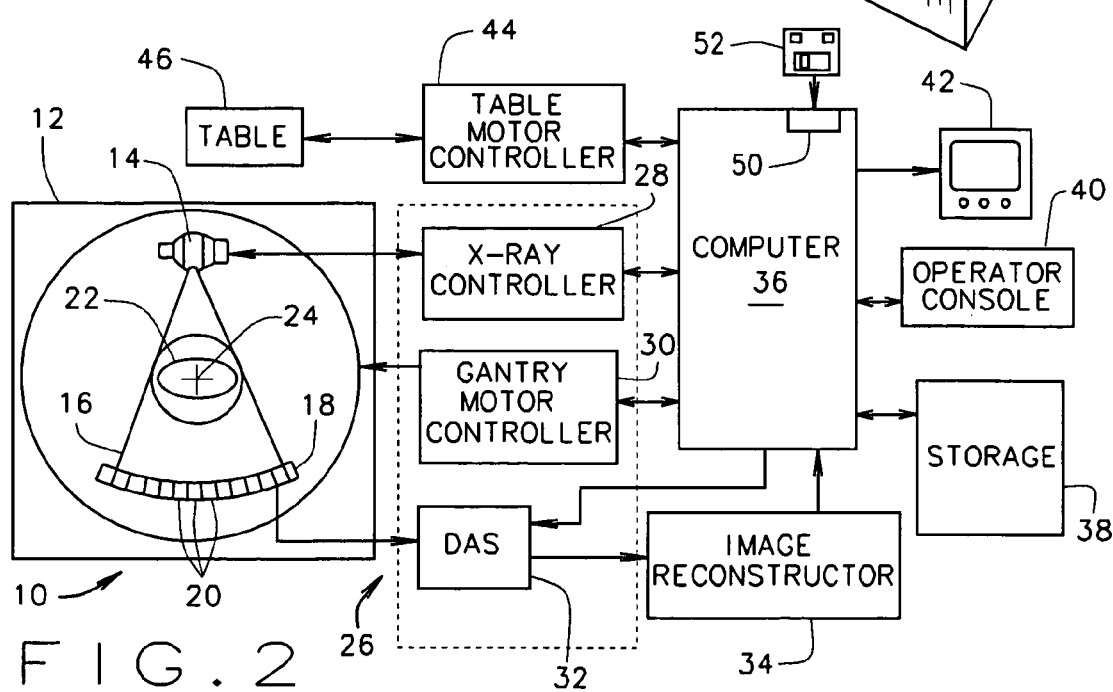
FIG. 2 is a block schematic diagram of the system illustrated in FIG. 1.

Referring to FIG. 1 and FIG. 2, a multi-slice scanning imaging system, for example, a Computed Tomography (CT) imaging system 10, is shown as including a gantry 12 representative of a "third generation" CT imaging system. Gantry 12 has a radiation source 14 which may be an x-ray tube 14 (also called x-ray source 14 herein) that projects a beam of radiation 16 toward a detector array 18 on the opposite side of gantry 12. (Configurations of the present invention are not limited to x-ray sources or x-ray radiation, although the configuration of CT imaging system 10 shown in FIG. 1 and FIG. 2 utilizes an x-ray source and x-ray radiation.) Detector array 18 is formed by a plurality of detector rows (not shown) including a plurality of detector elements 20 which together sense the radiation (i.e., in the configuration described herein, projected x-rays) that passes through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube or other type of display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a mass storage device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector-rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
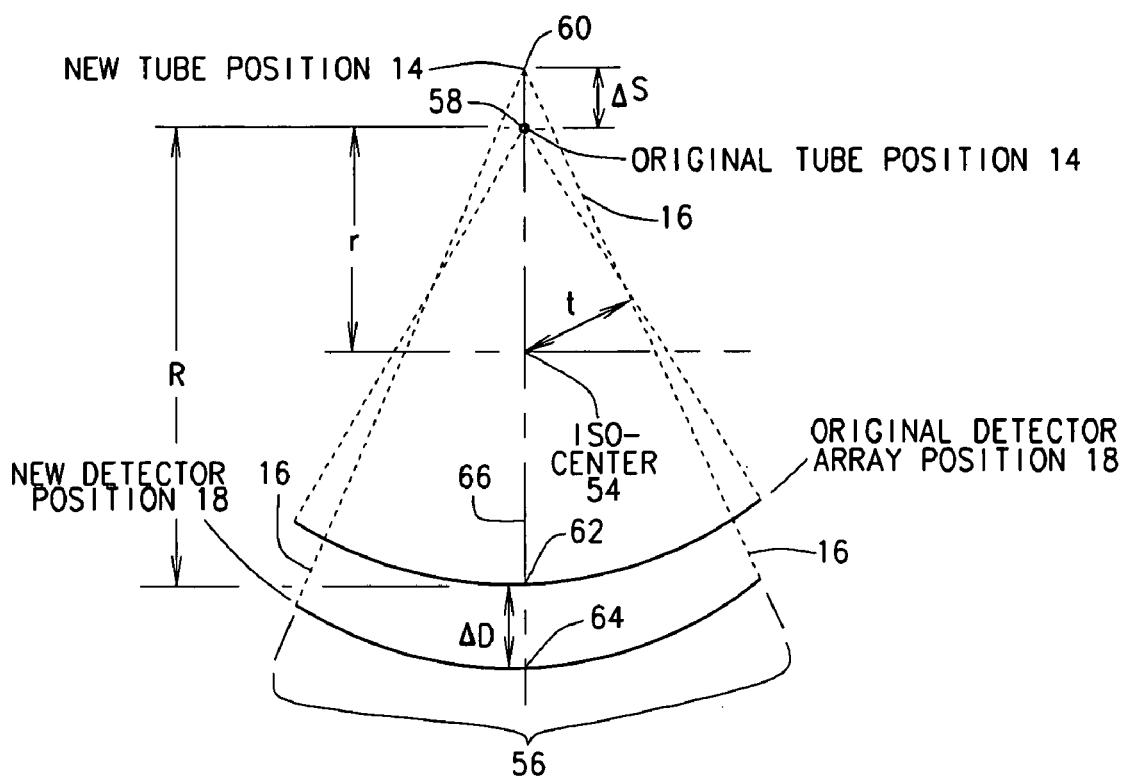
FIG. 3 is a representation of large bore geometry in which both the detector and the tube are positioned away from an isocenter.

In various configurations of the present invention and referring to FIG. 3, a technical effect of the present invention is the production of an image or images of a patient or object 22 in which artifacts in the image or images are reduced. The technical effect is achieved by a user scanning an object or patient 22 utilizing a CT imaging system 10 and operating CT imaging system 10 to reconstruct images of the scanned object.

Figure 6:
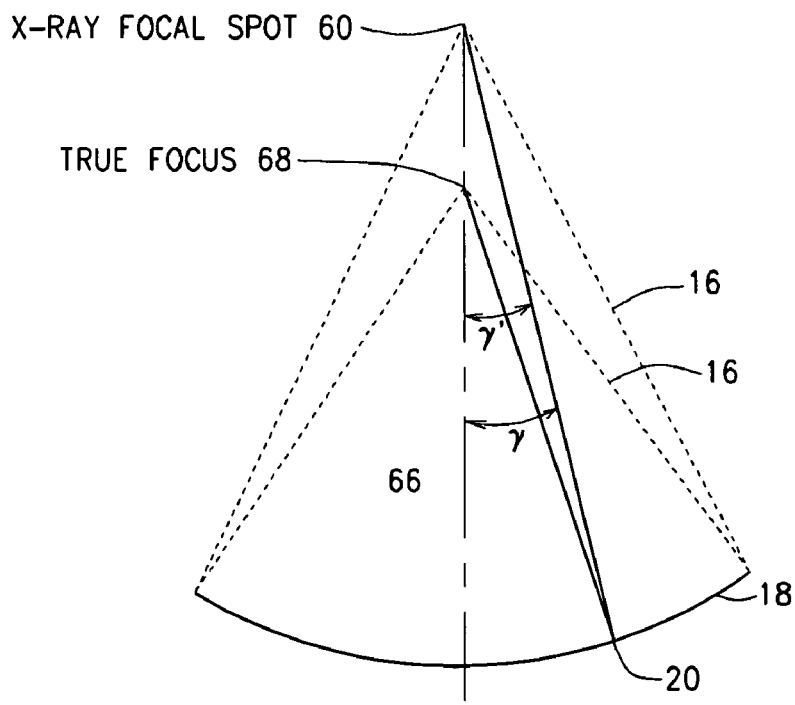
FIG. 6 is an illustration of a large bore geometry showing an x-ray focal spot out of focus, i.e., a fan angle corresponding to each detector element has changed relative to the nominal design of the detector array.
Figure 4:
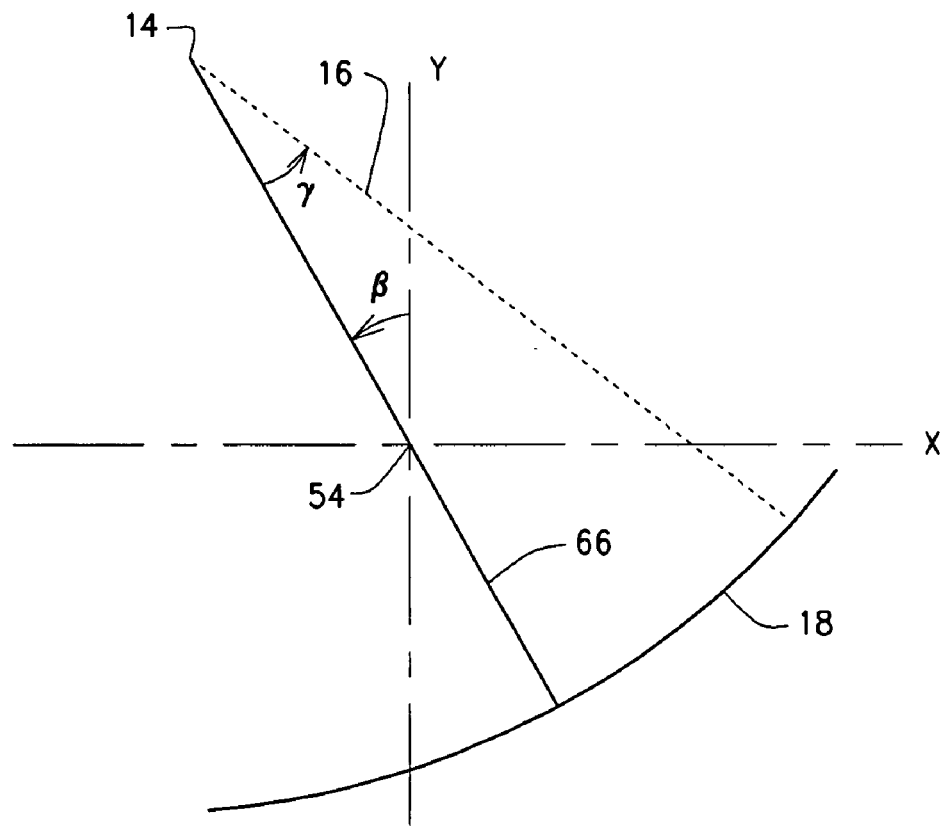
FIG. 4 is a further representation of the geometry of FIG. 3 showing additional variables.
Figure 5:
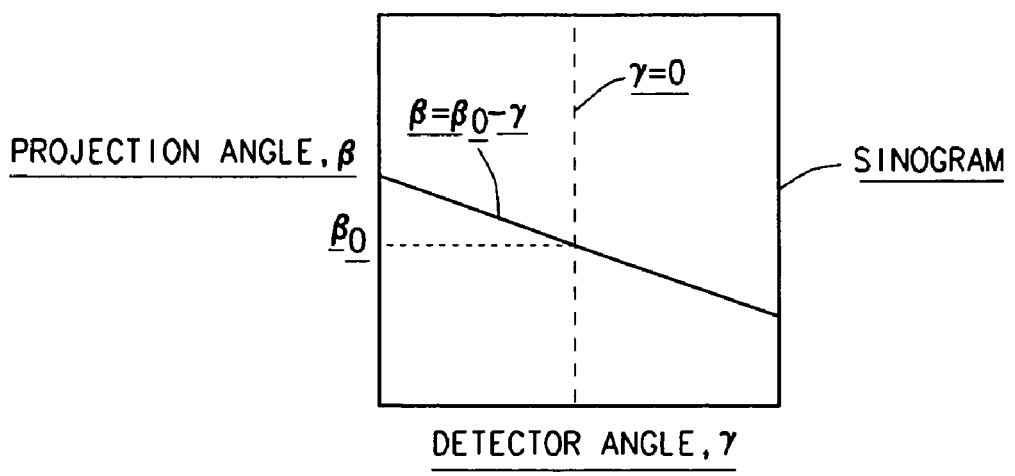
FIG. 5 illustrates a line on which interpolation of an original fan beam sinogram takes place in a rebinning process in some configurations.
Figure 7:
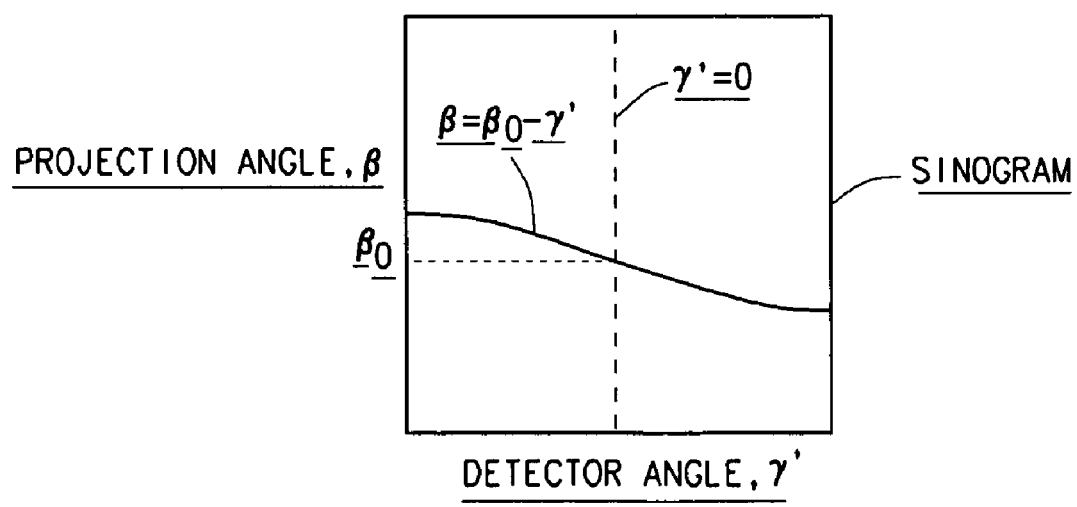
FIG. 7 illustrates a line on which fan to parallel beam rebinning takes place in some configurations in which a fan angle corresponding to each detector element is changed.

In some configurations of the present invention, a detector array 18 previously designed for the geometry of a first CT imaging system 10 having a first gantry opening 48 size is utilized in a second CT imaging system 10 having a different gantry opening 48 size. In second CT imaging system 10, both x-ray source 14 and detector array 18 are positioned an additional distance away from an isocenter 54 relative to the geometry of first CT imaging system 10 to thereby increase an operator's access. This positioning renders arc 56 of detector array 18 of imaging device 10 no longer concentric to a focal spot of the x-rays. For example, a focal spot of x-ray source 14 is moved from a first point 58 to a second point 60, and a center of detector array 18 in line with isocenter 54 is moved from a third point 62 to a fourth point 64. Some configurations of the present invention therefore rebin original fan beam 16 data into a set of parallel datasets prior to reconstruction in order to apply a geometric correction to the fan beam dataset. Referring to FIG. 3, FIG. 4, and FIG. 5, the rebinning process comprises interpolating an original fan beam 16 sinogram along a line defined by a relationship written as:

$$\beta = \beta_0 - \gamma \tag{1}$$

where $\beta_0$ is the angle of isoray 66, $\gamma$ is the detector fan angle and $\beta$ is the projection angle. When x-ray tube 14 and detector array 18 are moved back as illustrated in FIG. 6, the fan angle corresponding to each detector element 20 is changed relative to the nominal design of detector array 18. In general, the new angle, $\gamma'$, referenced to new tube 14 position 60 is smaller than the original angle $\gamma$, which is referenced relative to true focus 68 of detector array 18. The two angles $\gamma$ and $\gamma'$ are related by a relationship written as:

$$\gamma' = \tan^{-1}\left[\frac{R\sin\gamma}{R\cos\gamma + \Delta_s + \Delta_d}\right] \tag{2}$$

where R is the source 14 to detector element 20 distance in the original geometry (also the detector array 18 arc radius), and $\Delta_s$, and $\Delta_d$ are the distances x-ray source 14 and detector element 20 move back, respectively. Therefore, and referring to FIG. 7, the fan to parallel beam rebinning in some configurations takes place along a line represented by an equation written as:

$$\beta = \beta_0 - \gamma'. \tag{3}$$

Figure 8:
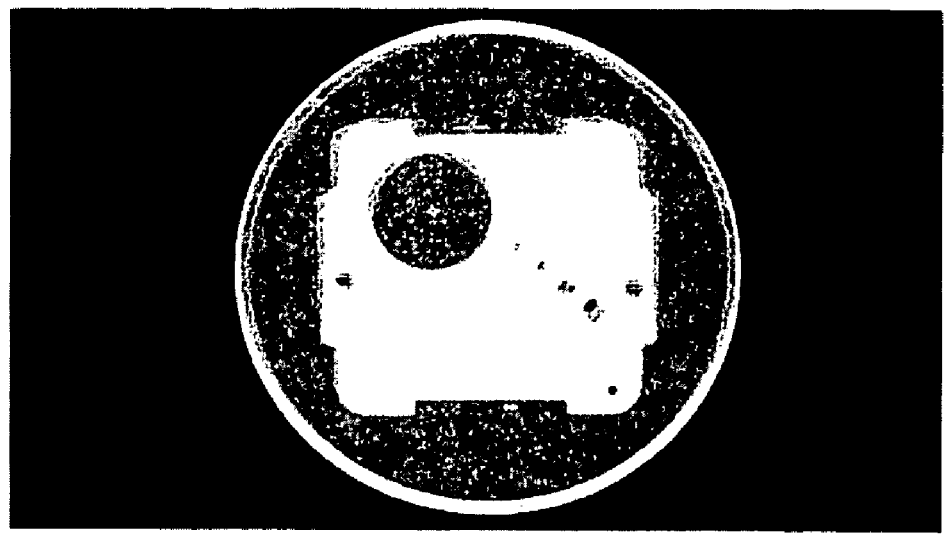
FIG. 8 is a prior art scan of a phantom using a CT imaging system in with a step-and-shoot mode without utilizing a compensation provided by configurations of the present invention.
Figure 9:
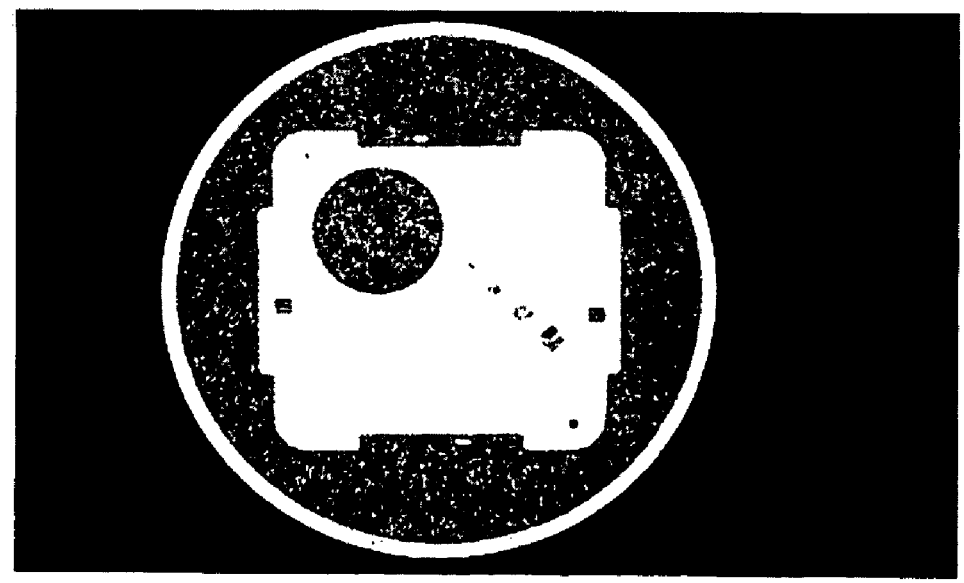
FIG. 9 is a scan of a phantom similar to that of FIG. 8 in which compensation is provided using a configuration of the present invention.

Some configurations of the present invention resample the parallel samples so that they are uniformly spaced. That is, the distance of each ray from isocenter 54 is determined, and the samples are interpolated to uniform space. The distance of each ray to isocenter 54, t, is determined in accordance with a relationship written as:

$$t = (r + \Delta_s)\sin\gamma', \tag{4}$$

where r is x-ray source 14 to isocenter 54 distance in the original geometry. During rebinning, the detector array 18 index s is determined from the distance t from isocenter 54 in accordance with a relationship written as:

$$s = \frac{1}{\Delta\gamma}\left\{\sin^{-1}\left[\frac{t}{r+\Delta_s}\right] + \sin^{-1}\left[\frac{(\Delta_s + \Delta_d)t}{R(r+\Delta_s)}\right]\right\} \tag{5}$$

where $\Delta\gamma$ is the fan angle between adjacent detector elements 20 in the original geometry. With adjustment, image artifacts and distortion are eliminated or significantly reduced, as shown by the contrast between FIG. 8 and FIG. 9.

In some configurations in which the fan beam reconstruction formula is used, the above relationships are used to provide a geometric correction to the fan beam dataset according to the corrected fan angle $\gamma'$ by first interpolating the fan beam data to a uniformly spaced fan beam dataset. The backprojection process is performed in accordance with the new geometry.

Figure 10:
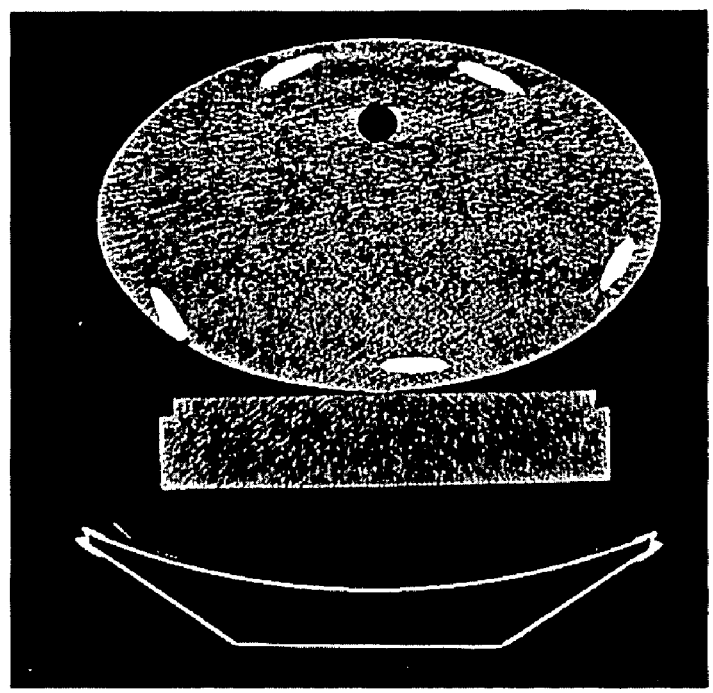
FIG. 10 is a prior art reconstructed images of a helical body phantom without utilizing helical weight adjustment configurations of the present invention.

Configurations of the present invention discussed above can be used with step-and-shoot scanning where no weighting function is applied, as well as configurations using step-and-shoot mode and in which a weighting function is applied. In configurations in which a weighting function is required for helical acquisition or halfscan, the original weighting function is adjusted to avoid artifacts. For illustration, FIG. 10 shows helically acquired data reconstructed without proper adjustment for the helical weights. Image artifacts are quite obvious.

Denoting the weighting function used in imaging apparatus 10 with original geometry by w($\gamma$, $\beta$, n), where n denotes the detector array 18 row index, a new weighting function, w', is derived from the original function by replacing $\gamma$ with $\gamma'$, where $\gamma'$ is defined as in equation (2):

$$w'=w(\gamma', \beta, n) \qquad (6)$$

Figure 11:
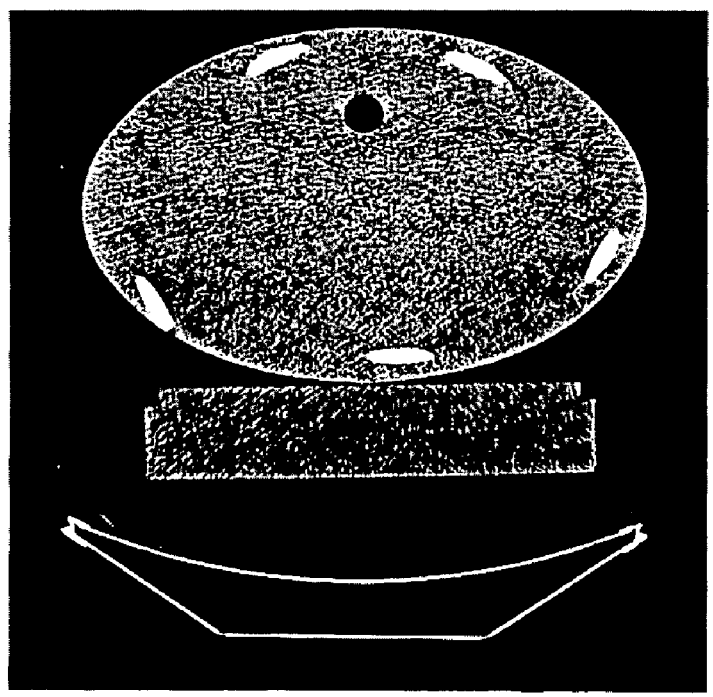
FIG. 11 is a reconstructed image of a helical body phantom similar to that of FIG. 10 in which a helical weight adjustment configuration of the present invention has been applied.

FIG. 11 shows the same scan reconstructed with the proper weighting function, demonstrating that the shading artifact is eliminated or substantially reduced.

Configurations of the present invention described above are single-slice configurations of CT imaging system 10 in which a fan beam dataset is used. However, many configurations of the present invention are also useful for multi-slice cone-beam datasets when a multi-slice detector array 18 is used. The equations and relationships described herein apply equally to single-slice and multiple-slice configurations, as well as to both fan beam datasets and cone beam datasets. Thus, more general configurations of the present invention can be described as operating on projection datasets rather than be limited either to either fan beam datasets or cone beam datasets.

It will thus be seen that configurations of the present invention are useful in reducing artifacts in reconstructed images when a larger gantry bore is desired. Development cost is reduced while maintaining the flexibility of an adjustable geometry by allowing a detector designed for the original geometry to be used. Image artifacts that would otherwise be introduced in reconstructed images are reduced by configurations of the present invention. More generally, it will be appreciated that configurations of the present invention are useful many cases in which an arc 56 of a detector array 18 of an imaging system 10 is not concentric to a focal spot of an x-ray source 14.

While the invention has been described in terms of various specific embodiments, those skilled in the art will recognize that the invention can be practiced with modification within the spirit and scope of the claims.

What is claimed is:

1. A method for reconstructing an image of an object of a computed tomographic imaging system having a detector array and a radiation source, wherein an arc of the detector array is not concentric to a focal spot of the radiation source, said method comprising:
    scanning the object with the computed tomographic imaging system to obtain a projection dataset;
    performing a geometric correction of the projection dataset according to a corrected fan angle; and
    reconstructing an image utilizing the corrected projection dataset.

2. A method in accordance with claim 1 wherein said performing a geometric correction comprises interpolating the projection dataset into a uniformly spaced projection dataset.

3. A method in accordance with claim 1 wherein said performing a geometric correction comprises rebinning the projection dataset into a set of parallel datasets.

4. A method in accordance with claim 3 wherein rebinning the projection dataset into a set of parallel datasets comprises interpolating a sinogram along a line defined by a relationship written as:

$$\beta=\beta_0-\gamma',$$

where:

$$\gamma' = \tan^{-1}\left[\frac{R\sin\gamma}{R\cos\gamma + \Delta_s + \Delta_d}\right]$$

and $\beta_0$ is an angle of an isoray of a radiation beam from the radiation source, $\gamma$ is a detector fan angle, $\beta$ is a projection angle, R is a radiation source to detector element distance in an original geometry in which an arc of the detector array is concentric to a focal spot of the radiation source, and $\Delta_s$, and $\Delta_d$ are distances that the radiation source and the detector element are from their respective positions in the original geometry, respectively.

5. A method in accordance with claim 3 further comprising resampling the parallel datasets so that the datasets are uniformly spaced.

6. A method in accordance with claim 5 wherein resampling the parallel datasets so that the datasets are uniformly spaced further comprises determining a distance of radiation rays to an isocenter.

7. A method in accordance with claim 6 wherein said distance of radiation rays to an isocenter is determined in accordance with a relationship written as:

$$t=(r+\Delta_s)\sin\gamma'$$

where t is the distance of a ray to the isocenter, r is the distance of the radiation source to the isocenter distance in an original geometry in which an arc of the detector array is concentric to a focal spot of the radiation source.

8. A method in accordance with claim 7 further comprising determining a detector array index s utilizing said distance t in accordance with a relationship written as:

$$s = \frac{1}{\Delta\gamma}\left\{\sin^{-1}\left[\frac{t}{r+\Delta_s}\right] + \sin^{-1}\left[\frac{(\Delta_s + \Delta_d)t}{R(r+\Delta_s)}\right]\right\}$$

where $\Delta\gamma$ is a fan angle between adjacent detector elements in the original geometry.

9. A method for reconstructing an image of an object of a computed tomographic imaging system having a detector array and a radiation source, wherein an arc of the detector array is not concentric to a focal spot of the radiation source, said method comprising:
    scanning the object with the computed tomographic imaging system to obtain a projection dataset;
    rebinning the projection dataset into a set of parallel datasets including interpolating a sinogram along a line defined by a relationship written as:

$$\beta=\beta_0-\gamma',$$

where:

$$\gamma' = \tan^{-1}\left[\frac{R\sin\gamma}{R\cos\gamma + \Delta_s + \Delta_d}\right]$$

and $\beta_0$ is an angle of an isoray of a radiation beam from the radiation source, $\gamma$ is a detector fan angle, $\beta_0$ is a projection angle, R is a radiation source to detector element distance in an original geometry in which an arc of the detector array is concentric to a focal spot of the radiation source, and $\Delta_s$ and $\Delta_d$ are distances that the radiation source and the detector element are from their respective positions in the original geometry, respectively;

resampling the parallel datasets so that the datasets are uniformly spaced; and reconstructing an image utilizing the set of resampled parallel datasets.

10. A method in accordance with claim 9 wherein resampling the parallel datasets so that the datasets are uniformly spaced further comprises determining a distance of radiation rays to an isocenter.

11. A method in accordance with claim 10 wherein said distance of radiation rays to an isocenter is determined in accordance with a relationship written as:

$$t = (r+\Delta_s)\sin\gamma'$$

where t is the distance of a ray to the isocenter, r is the distance of the radiation source to the isocenter distance in an original geometry in which an arc of the detector array is concentric to a focal spot of the radiation source.

12. A method in accordance with claim 11 further comprising determining a detector array index s utilizing said distance t in accordance with a relationship written as:

$$s = \frac{1}{\Delta\gamma}\left\{\sin^{-1}\left[\frac{t}{r+\Delta_s}\right] + \sin^{-1}\left[\frac{(\Delta_s+\Delta_d)t}{R(r+\Delta_s)}\right]\right\}$$

where $\Delta\gamma$ is a fan angle between adjacent detector elements in the original geometry.

13. A method for reconstructing an image of an object of a computed tomographic imaging system having a detector array and a radiation source, wherein an arc of the detector array is not concentric to a focal spot of the radiation source, said method comprising:

scanning the object using step-and-shoot scanning with the computed tomographic imaging system, without applying a weighting function, to obtain a projection dataset;

rebinning the projection dataset into a set of parallel datasets; and reconstructing an image utilizing the set of parallel datasets.

14. A method for reconstructing an image of an object of a computed tomographic imaging system having a detector array and a radiation source, wherein an arc of the detector array is not concentric to a focal spot of the radiation source, said method comprising:

scanning the object with the computed tomographic imaging system using helical or halfscan acquisition to obtain a projection dataset;

weighting the projection dataset in accordance with a weighting function w', derived from a weighting function w for an original geometry in which the arc of the detector array is concentric to the focal spot of the radiation source, wherein $$w' = w(\gamma', \beta, n)$$

and $$\gamma' = \tan^{-1}\left[\frac{R\sin\gamma}{R\cos\gamma + \Delta_s + \Delta_d}\right]$$

wherein $\gamma$ is a detector fan angle, $\beta$ is a projection angle, R is a radiation source to detector element distance in the original geometry, and $\Delta_s$ and $\Delta_d$ are distances that the radiation source and the detector element are from their respective positions in the original geometry, respectively;

rebinning the projection dataset into a set of parallel datasets; and reconstructing an image utilizing the set of parallel datasets.

15. A computed tomography imaging system having a detector array and an radiation source, wherein an arc of the detector array is not concentric to a focal spot of the radiation source, said imaging system configured to:

scan an object to obtain a projection dataset;

perform a geometric correction of the projection dataset according to a corrected fan angle; and reconstruct an image utilizing the corrected projection dataset.

16. A system in accordance with claim 15 wherein to perform a geometric correction, said system is configured to interpolate the projection dataset into a uniformly spaced projection dataset.

17. A system in accordance with claim 15 wherein to perform a geometric correction, said system is configured to rebin the projection dataset into a set of parallel datasets.

18. A system in accordance with claim 17 wherein to rebin the projection dataset into a set of parallel datasets, said system is configured to interpolate a sinogram along a line defined by a relationship written as:

$$\beta = \beta_0 - \gamma',$$

where:

$$\gamma' = \tan^{-1}\left[\frac{R\sin\gamma}{R\cos\gamma + \Delta_s + \Delta_d}\right]$$

and $\beta_0$ is an angle of an isoray of a radiation beam from the radiation source, $\gamma$ is a detector fan angle, $\beta$, is a projection angle, R is a radiation source to detector element distance in an original geometry in which an arc of the detector array is concentric to a focal spot of the radiation source, and $\Delta_s$, and $\Delta_d$ are distances that the radiation source and the detector element are from their respective positions in the original geometry, respectively.

19. A system in accordance with claim 17 further configured to resample the parallel datasets so that the datasets are uniformly spaced.

20. A system in accordance with claim 19 wherein to resample the parallel datasets so that the datasets are uniformly spaced, said system is further configured to determine a distance of radiation rays to an isocenter.

21. A system in accordance with claim 20 configured to determine said distance of radiation rays to an isocenter in accordance with a relationship written as:

$$t = (r+\Delta_s)\sin\gamma'$$

where t is the distance of a ray to the isocenter, r is the distance of the radiation source to the isocenter distance in an original geometry in which an arc of the detector array is concentric to a focal spot of the radiation source.

22. A system in accordance with claim 21 further configured to determine a detector array index s utilizing said distance t in accordance with a relationship written as:

$$s = \frac{1}{\Delta\gamma}\left\{\sin^{-1}\left[\frac{t}{r+\Delta_s}\right] + \sin^{-1}\left[\frac{(\Delta_s+\Delta_d)t}{R(r+\Delta_s)}\right]\right\}$$

where $\Delta\gamma$ is a fan angle between adjacent detector elements in the original geometry.

23. A computed tomography imaging system having a detector array and a radiation source, wherein an arc of the detector array is not concentric to a focal spot of the radiation source, said imaging system configured to:
  scan the object to obtain a projection dataset;
  rebin the projection dataset into a set of parallel datasets including interpolating a sinogram along a line defined by a relationship written as:

$\beta = \beta_0 - \gamma'$, where:

$$\gamma' = \tan^{-1}\left[\frac{R\sin\gamma}{R\cos\gamma + \Delta_s + \Delta_d}\right]$$

and $\beta_0$ is an angle of an isoray of a radiation beam from the radiation source, $\gamma$ is a detector fan angle, $\beta$ is a projection angle, R is a radiation source to detector element distance in an original geometry in which an arc of the detector array is concentric to a focal spot of the radiation source, and $\Delta_s$ and $\Delta_d$ are distances that the radiation source and the detector element are from their respective positions in the original geometry, respectively;
  resample the parallel datasets so that the datasets are uniformly spaced; and
  reconstruct an image utilizing the set of resampled parallel datasets.

24. A system in accordance with claim 23 wherein to resample the parallel datasets so that the datasets are uniformly spaced, said system is further configured to determine a distance of radiation rays to an isocenter.

25. A system in accordance with claim 24 configured to determine said distance of radiation rays to an isocenter in accordance with a relationship written as:

$t = (r+\Delta_s)\sin\gamma'$ where t is the distance of a ray to the isocenter, r is the distance of the radiation source to the isocenter distance in an original geometry in which an arc of the detector array is concentric to a focal spot of the radiation source.

26. A system in accordance with claim 25 further configured to determine a detector array index s utilizing said distance t in accordance with a relationship written as:

$$s = \frac{1}{\Delta\gamma}\left\{\sin^{-1}\left[\frac{t}{r+\Delta_s}\right] + \sin^{-1}\left[\frac{(\Delta_s+\Delta_d)t}{R(r+\Delta_s)}\right]\right\}$$

where $\Delta\gamma$ is a fan angle between adjacent detector elements in the original geometry.

27. A computed tomography imaging system having a detector array and a radiation source, wherein an arc of the detector array is not concentric to a focal spot of the radiation source, said imaging system configured to:
  scan the object using step-and-shoot scanning without applying a weighting function to obtain a projection dataset;
  rebin the projection dataset into a set of parallel datasets; and
  reconstruct an image utilizing the set of parallel datasets.

28. A computed tomography imaging system having a detector array and a radiation source, wherein an arc of the detector array is not concentric to a focal spot of the radiation source, said imaging system configured to:
  scan the object using helical or halfscan acquisition to obtain a projection dataset;
  weight the projection dataset in accordance with a weighting function w', derived from a weighting function w for an original geometry in which the arc of the detector array is concentric to the focal spot of the radiation source, wherein $w' = w(\gamma', \beta, n)$ and $$\gamma' = \tan^{-1}\left[\frac{R\sin\gamma}{R\cos\gamma + \Delta_s + \Delta_d}\right]$$

wherein $\gamma$ is a detector fan angle, $\beta$ is a projection angle, R is a radiation source to detector element distance in the original geometry, and $\Delta_s$, and $\Delta_d$ are distances that the radiation source and the detector element are from their respective positions in the original geometry, respectively;
  rebin the projection dataset into a set of parallel datasets; and
  reconstruct an image utilizing the set of parallel datasets.

* * * * *

UNITED STATES PATENT AND TRADEMARK OFFICE
CERTIFICATE OF CORRECTION

PATENT NO. : 6,944,260 B2 Page 1 of 1
APPLICATION NO. : 10/705357
DATED : September 13, 2005
INVENTOR(S) : Hsieh et al.

It is certified that error appears in the above-identified patent and that said Letters Patent is hereby corrected as shown below:

In Claim 9, column 8, line 67, delete " $\beta_0$ is a projection" and insert therefor -- $\beta$ is a projection--.

Signed and Sealed this

Thirteenth Day of November, 2007

JON W. DUDAS
*Director of the United States Patent and Trademark Office*